United States Patent [19]
Yamaguchi et al.

[11] Patent Number: 6,107,515
[45] Date of Patent: Aug. 22, 2000

[54] PROCESS FOR PREPARING METHACRYLIC OR ACRYLIC ESTERS

[75] Inventors: Tatsuo Yamaguchi, Shizuoka; Hiroshige Okamoto, Okayama, both of Japan

[73] Assignee: Asahi Kasei Kogyo Kabushiki Kaisha, Osaka, Japan

[21] Appl. No.: 09/254,553

[22] PCT Filed: Sep. 9, 1997

[86] PCT No.: PCT/JP97/03173

§ 371 Date: Mar. 10, 1999

§ 102(e) Date: Mar. 10, 1999

[87] PCT Pub. No.: WO98/11050

PCT Pub. Date: Mar. 19, 1998

[30] Foreign Application Priority Data

Sep. 10, 1996 [JP] Japan ................................. 8-238863

[51] Int. Cl.⁷ ................................................. C07C 67/02
[52] U.S. Cl. ........................... 560/261; 560/208; 562/234
[58] Field of Search ............................. 562/534; 560/208, 560/261

[56] References Cited

U.S. PATENT DOCUMENTS 5,248,427 9/1993 Spiske et al. .

FOREIGN PATENT DOCUMENTS

| 0584411 | 3/1994 | European Pat. Off. . |
| 58-198442 | 11/1983 | Japan . |
| 2730 | 1/1990 | Japan . |
| 478626 | 12/1992 | Japan . |
| 5201930 | 8/1993 | Japan . |

*Primary Examiner*—Paul J. Killos
*Assistant Examiner*—Robert W. Deemie
*Attorney, Agent, or Firm*—Birch, Stewart, Kolasch & Birch, LLP

[57] ABSTRACT

A process for producing a methacrylic acid ester or an acrylic acid ester comprising: reacting methacrolein or acrolein with an alcohol or molecular oxygen in the presence of a catalyst comprising Pd; removing water with a separation membrane which can selectively permeate water from a mixed liquid of the alcohol and water.

4 Claims, 1 Drawing Sheet

PROCESS FOR PREPARING METHACRYLIC OR ACRYLIC ESTERS

This application is the national phase under 35 U.S.C. §371 of prior PCT International Application No. PCT/JP97/03173 which has an International filing date of Sep. 9, 1997 which designated the United States of America.

TECHNICAL FIELD

This invention relates to a process for producing a methacrylic acid ester or an acrylic acid ester from methacrolein or acrolein, and an alcohol and molecular oxygen in the presence of a catalyst comprising Pd.

BACKGROUND ART

A new route is now being spotlighted for producing, in one step, a methacrylic acid ester or an acrylic acid ester by reacting methacrolein or acrolein with an alcohol and molecular oxygen. This reaction is effected by reacting methacrolein or acrolein with molecular oxygen in an alcohol, in the presence of a catalyst comprising Pd.

This reaction produces water in a similar manner as the conventional esterification reaction using a carboxylic acid and an alcohol. Some of the water produced competes with the alcohol to react with an aldehyde, to produce a carboxylic acid as a by-product, and consequently, the selectivity of a carboxylic acid ester is lowered. Also, products such as water, carboxylic acids and the like are considered to be easily adsorbed on the active site of the catalyst, thereby increasingly reducing the reaction rate as the concentrations of water and carboxylic acid increases. Therefore, attempting to increase the productivity by increasing the aldehyde concentration without changing the catalyst amount, results in decreasing the reaction rate.

An approach to solving the above-mentioned problems associated with high productivity in the presence of high concentrations of an aldehyde has been to replace the reactor with a multi-stage reactor. More-over, a method in which the reaction is effected while water is removed from the reaction system has been proposed in JP-B-4-78,626. In this reference, it is disclosed that the reaction is effected while molecular sieves, which are general water-adsorbents, and the like are added to the reaction system as a means for removing water. According to this method, conversion is not reduced even at a high aldehyde concentration, and a high selectivity of methyl methacrylate or methyl acrylate is shown.

However, the present inventors have found that in order to continuously carry out the reaction by this method, recycling of the molecular sieves is indispensable, that is, the used molecular sieves are taken out of the reaction system, regenerated, and introduced again into the reaction system. The operation of recycling the absorbent on a commercial scale results in a reduction of the running operability, and when the adsorbed water is removed in the course of regenerating the absorbent, some of the methacrylic acid ester or acrylic acid ester produced by the reaction is removed together with the water, resulting in a reduction in yield. Accordingly, this method in which an absorbent, such as a molecular sieve or the like, is used is effective when the method is carried out on a small scale for a short period of time. However, when the method is carried out on a commercial scale, not only is there the need for absorbent-regenerating process equipment, but also there is product lost during the regenerating process. Furthermore, the above-mentioned method is ideally suited for a batch operation, and hence, is problematic when a continuous reaction is carried out for a long period of time.

On the other hand, the present inventors have examined a method using reaction-distillation in which azeotropic distillation with water is effected; however, the complete separation of the starting aldehyde and alcohol from the objective carboxylic acid ester has been difficult, and it has been difficult to selectively separate only water by distillation. That is to say, by the conventional technique, it has been difficult to continue the reaction while continuously removing water from the reaction system on a commercial scale.

DISCLOSURE OF THE INVENTION

In consideration of the state of the art, the present inventors have researched a process for producing a methacrylic acid ester or an acrylic acid ester which process is high in selectivity for the objective product and can be carried out on a commercial scale. As a result, they have found that water can be separated from the reaction system by using a functional separation membrane which selectively permeates water from a mixed liquid of an alcohol with water. Thereby completing the invention by which a methacrylic acid ester or an acrylic acid ester can be stably and continuously produced while water is continuously removed.

That is to say, an embodiment of this invention is a process for producing a methacrylic acid ester or an acrylic acid ester by reacting methacrolein or acrolein with an alcohol and molecular oxygen in the presence of a catalyst comprising Pd, wherein the reaction is effected while water is removed through a separation membrane which can selectively permeate water from a mixed liquid of an alcohol and water.

This invention aims at economically providing a carboxylic acid ester with high selectivity and productivity by such a production process.

The separation of a mixture of at least two liquids, which have close boiling points, by distillation is difficult, and the separation of an azeotropic mixture of liquids having the same boiling point by distillation is impossible, and hence, research on a functional membrane which can be used for the separation of them has heretofore been made. However, in the reaction system for producing a methacrylic acid ester or an acrylic acid ester according to this invention, it is necessary to separate water from a mixed liquid comprising many kinds of organic materials such as an aldehyde, for example, methacrolein, acrolein or the like; an alcohol; a methacrylic acid ester or an acrylic acid ester; and a carboxylic acid ester, and in view of the complexity of membrane separation of an organic liquid mixture, it is difficult to predict the type of membrane useful for separating water. Therefore, no membrane has heretofore been used for water separation in such a reaction system. The present invention includes the separation of water from a reaction system of a methacrylic acid ester or an acrylic acid ester by use of a functional separation membrane which selectively permeates water from a mixed liquid of water with an alcohol as mentioned above.

According to the process of the present invention, unlike the conventional process using an adsorption method, it is possible to continuously remove water at a rate such that the water concentration can be maintained low and constant. Accordingly, it has become possible to obtain a methacrylic acid ester or an acrylic acid ester with a high selectivity and simultaneously maintain over a long period of time, a higher reaction rate than has been shown by conventional methods. Moreover, since the reaction conditions are maintained constant, the amount of alkali necessary to neutralize the carboxylic acid produced (owing to the water produced as a by-product) can be sharply reduced. In addition, though this alkali is neutralized again with sulfuric acid in the purification process and thereafter removed as a waste, even in this case, the amount of the sulfuric acid used there and the amounts of the neutralization product, sodium sulfate, can also be reduced. Furthermore, since the amounts of the carboxylic acid or the alkali and the like used in the neutralization are reduced, the load applied to a catalyst is decreased and the catalyst life is prolonged. Therefore, the positive effects obtained by water-removal in the present invention is very great.

BEST MODE FOR CARRYING OUT THE INVENTION

Figure 1:
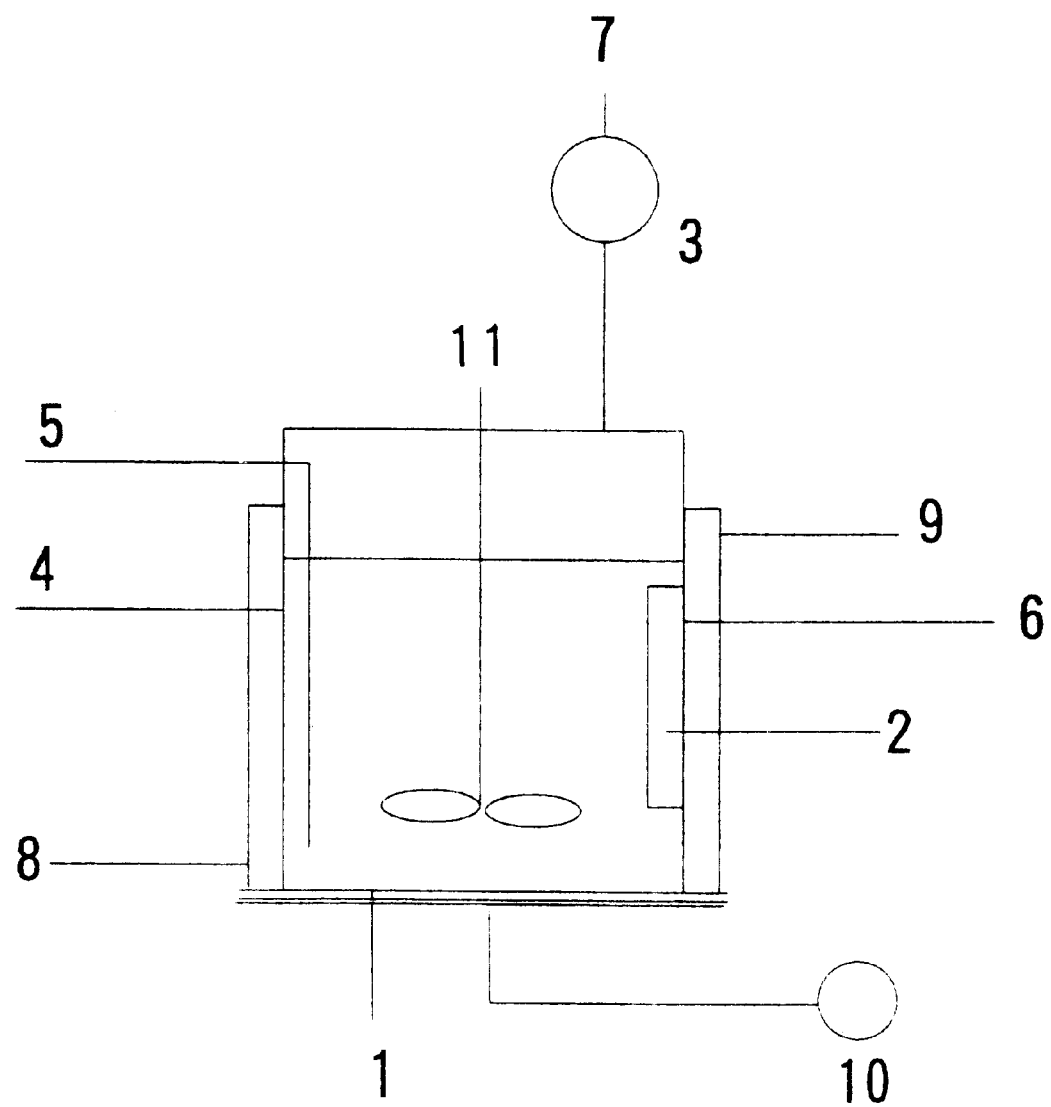
FIG. 1 is a conceptual view of an example of the reaction apparatus used in this invention.

In this invention, what can be used as a water-separation membrane is a separation membrane which can selectively permeate water from a mixed liquid of an alcohol with water. As separation membranes having excellent characteristics for separating water from an alcohol, there are 1) a membrane which separates the alcohol component by selective permeation and 2) a membrane which separates water by selective permeation. Preferably the membrane which selectively separates water is used.

A water separation membrane is selected based on parameters including shape of the reactor, and the like. Organic membranes include, but are not limited to a polyhydroxymethylene membrane, an acrylic acid-acrylonitrile copolymer membrane, an ionized chitosan membrane, a composite membrane in which a PVA active layer crosslinked with maleic acid is provided and a polymer alloy membrane as mentioned respectively in JP-A-59-109,204 and JP-A-60-129,104, and the like; inorganic membranes such as an A type zeolite membrane as stated in Chemical Engineering Symposiums, Vol. 41, pages 102–105 (1994) and the like. Also included are organic and inorganic membranes which have been known as water-ethanol separation membranes.

From an industrial perspective, the membrane ideally has excellent durability and excellent chemical resistance to the reaction mixture which comprises both acidic materials and alkaline materials, which are fed for neutralizing the said acidic materials, and the like; also it keeps a sufficient mechanical strength to resist mixing for the three-phase-mixing of a gas, a liquid and a solid; and the like. Inorganic membranes are generally functional at high working temperatures and have excellent chemical resistance.

In the reaction system, swelling of the water-separation membrane with methacrolein and acrolein may take place. Therefore it is preferable to use water-separation membranes that are high in resistance to swelling with methacrolein and acrolein and whose membrane performance (separation factor, permeation flux and the like) is not changed even after a long time, for example, 100 hours, has elapsed. It is preferable that the water-separation coefficient ($\alpha$) in the reaction system, in which methacrolein or acrolein is present, is at least 1,000 and the permeation flux is large. Inorganic membranes having a permeation flux (Q) of at least 0.01, specifically an A type zeolite membrane and the like are preferably used.

Incidentally, the separation membrane of the present invention which is used in the reaction system for producing various methacrylic acid esters or acrylic acid esters from methacrolein or acrolein and various alcohols, and the above-mentioned water-separation coefficient ($\alpha$) and permeation flux (Q) are determined under the following conditions:

when using a separation membrane having a membrane area of 0.01 m$^2$, a solution consisting of 15% by weight of methacrolein, 15% by weight of methyl methacrylate, 65% by weight of methanol and 5% by weight of water is initially vacuum pumped from the permeation side at a temperature of 80° C. and an absolute pressure of 3 kg/cm$^2$ for 100 hours and is subjected to pervaporation separation, the following equation is obtained:

$$\alpha_{AB} = (Y_A/Y_B)*(X_B/X_A)$$

wherein A represents water, B represents the other components, $X_A$ and $X_B$ represent the weight fractions of water A and the other components B on the liquid-feeding side, respectively, and $Y_A$ and $Y_B$ represent the weight fractions of water A and the other components B on the permeation side as $Y_A$ and $Y_B$ respectively.

Also, the permeation flux is the permeation weight per unit membrane area per hour and is indicated by the following equation:

$$Q = \text{(weight of the overall components on the permeation side)}/0.01*100 (Kg/m^2 \cdot h).$$

The above-mentioned A type zeolite membrane can be obtained, (as mentioned in Chemical Engineering Symposiums, Vol. 41, pages 102–105 (1994)) by immersing a porous aluminum support having a pore diameter of about 1 $\mu$m as a substrate in a mixed solution comprising sodium silicate, sodium hydroxide, sodium aluminate and aluminum hydroxide having such a composition that $H_2O/Na_2O=60$, $Na_2O/SiO_2=1$ and $SiO_2/Al_2O_3=2$, and thereafter subjecting them to a hydrothermal reaction at a temperature of 80–100° C. for 3–12 hours. Incidentally, by repeating the immersion and the hydrothermal reaction, it is possible to adjust and control the characteristics of the membrane.

The shape, size and the like of the separation membrane are varied depending upon the size of the reactor and are set depending upon the amount of water to be produced by the reaction of an aldehyde with an alcohol or the like, the amount of water to be removed and the membrane performance.

The separation membrane can be formed into various shapes by selecting the shape of the substrate and any shape can be selected according to the structure of the reactor. For example, flat membrane, modularized flat membrane, cylindrical membrane, modularized cylindrical membrane and the like are generally used.

The water-removing functional portion of the separation membrane may be installed into the line where the reaction mixture is recycled, thereby returning to the reactor, the reaction mixture from which water has been separated and removed. Alternatively, it may be installed directly in the interior of the reactor, or may be set in both the reaction mixture-recycling line and the interior of the reactor. It is preferable to select an appropriate method depending upon the conditions and carry out the same.

As the mode in which the water-removing functional portion is installed directly in the interior of the reactor, for example, FIG. 1 is mentioned. In this mode, the starting materials and air are fed through a starting materials-feeding line 4 and an air-feeding line 5, respectively, to the reactor which is maintained at a constant temperature with a heat transfer medium fed from a heat transfer medium-feeding line 8, and the reaction mixture is taken out from a reaction mixture-withdrawing port 6. In the lower part of the reactor, a water-separation membrane 1 is installed so as to contact the reaction mixture side, so that by creating a negative pressure on the opposite side of the membrane by a vacuum pump 10 (a pervaporation (PV) method), it is possible to carry out the reaction continuously while removing water. In FIG. 1, 2 refers to a catalyst-separating filter, 3 to cooling condenser, 7 to a vent line, 9 to a heat transfer medium-withdrawing line and 11 to a stirrer.

When removing water, a high temperature is advantageous from the viewpoint of water-permeating rate, but a low temperature is advantageous from the viewpoint of water-separating performance. The temperature can be selected in the range of from room temperature to 200° C. When the water-removing functional portion is incorporated into the reaction system as a part of the reactor, the reaction temperature is selected from the range of 50–160° C., preferably from the range of 70–120° C.

When the operating pressure for separating water is set to create a pressure difference between both sides of the membrane, water-separating operation is possible. The pressure is usually set in the range of 0.5–20 $Kg/cm^2$. When the operating pressure is, for example, 5 $Kg/cm^2$, water can be separated even if the pressure on the opposite side of the membrane is the normal pressure, but in this case, the flow rate is small. Therefore, it is preferable to use a vacuum, since water can be removed more effectively.

In the present invention, it is ideal to remove the water until the amount of the remaining water approaches zero, with respect to production rate (reaction rate) and selectivity; however, for this to be possible, a vast membrane area becomes necessary, which is not economical. The effect of water removal varies depending upon the kinds of aldehyde and alcohol to be reacted and the reaction conditions, so that the ideal degree of water removal is not constant for system to system. By removing ½ of the concentration of water produced, an about double productivity can be obtained. Therefore, the preferable amount of water remaining in the reaction mixture is ½ of the amount of water produced, and the more preferable amount is ⅓–1/10. Furthermore, the effect is further increased by reducing the amount to 1/100 or less; however, as mentioned above, in view of the production cost of membrane and equipment costs such as installation space or the like, the preferable range is from ⅓ to 1/10.

The catalyst used in the reaction is a palladium-containing supported catalyst. Preferably, the catalyst contains palladium and lead, and more preferably, a specific palladium-lead intermetallic compound is used. A catalyst which satisfies the conditions shown in Examples appearing hereinafter is much more preferable. As different elements from palladium and lead, there may be contained Hg, Tl, Bi, Te, Ni, Cr, Co, Cd, In, Ta, Cu, Zn, Zr, Hf, W, Mn, Ag, Re, Sb, Sn, Rh, Ru, Ir, Pt, Au, Ti, Al, B, Si and the like.

The catalyst carrier can be broadly selected from silica, alumina, silica-alumina, zeolite, magnesia, magnesium hydroxide, titania, calcium carbonate, activated carbon and the like.

The amount of palladium supported on a carrier is not particularly limited; however, it is usually 0.1–20% by weight, preferably 1–10% by weight, based on the weight of the carrier. The amount of lead supported is neither particularly limited and is usually 0.1–20% by weight, preferably 1–10% by weight. The supported composition ratio (atomic ratio) of palladium/lead is rather important than the amount of each of palladium and lead supported. The supported composition ratio (atomic ratio) of palladium/lead is 3/3–3/0.9, preferably 3/2 to 3/0.9, and more preferably 3/1.3 to 3/0.9. The elements other than palladium and lead are in the range of 0–5% by weight, preferably not more than 1% by weight.

The amount of the catalyst varies greatly and depends upon the kinds of the reactants, the composition of catalyst, the method of preparing catalyst, the reaction conditions, the reaction type and the like and is not particularly limited; however, when the catalyst is reacted in the slurry state, it is preferable to use the same in a proportion of 0.04–0.5 kg per one liter of the reaction mixture.

An explanation is made below of the present process for continuously producing a methacrylic acid ester or an acrylic acid ester.

Acrolein and methacrolein which are the starting aldehydes used can be used alone or in an admixture.

The starting alcohol is not particularly limited, and various alcohols can be used as the reactant. Aliphatic alcohols, aromatic alcohols and the like can be used. Specifically, in the case of the production of a methacrylic acid ester, methanol is used and in the case of an acrylic acid ester, methanol, ethanol, n-butanol, 2-ethylhexanol and the like are used, whereby the corresponding esters such as methyl methacrylate, methyl acrylate, ethyl acrylate, butyl acrylate, 2-ethylhexyl acrylate and the like can be obtained, respectively.

The ratio of the amounts of the aldehyde and alcohol used is not particularly limited, and can be selected in such a broad range that, for example, the aldehyde/alcohol mole ratio is 10/1–1/1,000; however, in general, it is selected in the range of 1/1–1/50. More-over, in this invention, even when the aldehyde concentration is high and in the range of 2/1–1/4, it is possible to realize a sufficiently high selectivity of methacrylic acid ester or acrylic acid ester.

The production of a methacrylic acid ester or an acrylic ester can be carried out by any method which has heretofore been known and in which a gas phase reaction, a liquid phase reaction, an irrigation reaction or the like is used. For example, when the reaction is effected in the liquid phase, the production can be carried out in any type of reactor such as a bubble column type reactor, a draft tube type reactor, a stirring bath type reactor or the like in which a water-selective separation membrane is installed.

Oxygen used in the production of a methacrylic acid ester or an acrylic acid ester can be used in the form of molecular oxygen, namely oxygen gas per se, or in the form of a mixed gas in which an oxygen gas is diluted with a diluent inert to the reaction, for example, nitrogen, carbonic acid gas or the like. As the source of oxygen, air can also be used. The oxygen partial pressure on the outlet side of the reactor is preferably 0.4 $kg/cm^2$ or less though it varies depending upon the kinds of reactants, the reaction conditions, the type of reactor and the like. The oxygen partial pressure can be adjusted to not more than 0.2 $kg/cm^2$, however when oxygen pressure is too low, the conversion of the starting aldehyde is lowered and troublesome by-products are produced, so that the oxygen partial pressure should be selected from such a range so as to minimize these adverse effects.

The reaction pressure can be selected from any broad pressure range of from under reduced pressure to under pressure. Usually, however, it is selected from the range of 0.5–20 $kg/cm^2$. It is better to set the total pressure so that the oxygen concentration in the gas discharged from the reactor does not exceed the explosion limit (8%).

For the production of a methacrylic acid ester or an acrylic acid ester, it is preferable to keep the pH in the reaction system at 6–9 by adding to the reaction system an alkali metal compound or an alkaline earth metal compound (for example, oxide, hydroxide, carbonate, carboxylic acid salt or the like). The compounds of these alkali metals or alkaline earth metals can be used alone or in combination.

The reaction time is not particularly limited, and varies depending upon the set conditions, so that it cannot be uniquely determined. It is usually, however, 0.5–20 hours.

The present invention is illustrated with the following Examples and Comparative Examples and is not particularly limited thereto. Incidentally, the pressure used in Examples and the like is shown by absolute pressure and indicated in kg/cm$^2$.

The palladium-containing catalyst used in the reaction is preferably a palladium-lead intermetallic compound satisfying the specific conditions and is a $Pd_3Pb_1$ intermetallic compound, the main peak of which is within the range of 2θ=38.55–38.70 degree as measured by the X-ray diffraction mentioned below, is preferred from the viewpoint of catalyst performance. Accordingly, a preferable catalyst was prepared according to the preparation method shown in the following Reference Production Example. Also, the measurement of the $Pd_3Pb_1$ intermetallic compound by the X-ray diffraction was required to be conducted with good precision and hence carried out according to the measurement procedure mentioned below. The catalyst was subjected to measurement after it was vacuum exhausted at 160° C. and then treated for 3 hours to remove the low molecular weight adsorbed/occluded components.

Measurement of X-ray Diffraction Angle on the (111) Face of Palladium-Lead Intermetallic Compound Using an X-ray diffraction apparatus Model RAD-RA manufactured by Rigaku Denki K. K., the diffraction angle 2θ on the (111) face of a palladium/lead intermetallic compound which was a supported catalyst was measured according to the conventional measurement procedure for powder X-ray diffraction using CuKα1 ray (1.540–5981). The measurement must be effected with particularly high precision. The (111) face and (200) face of the $LaB_6$ compound defined as the standard reference material 660 in, for example, National Institute of Standards & Technology were measured and standardized so that the respective peak values became 2θ=37.441 degree and 43.506 degree, whereby results with high measurement precision and good reproducibility are obtained.

REFERENCE PRODUCTION EXAMPLE 1

Aluminum nitrate and magnesium nitrate were add to and dissolved in SNOWTEX N-30 (a trade name of Nissan Chemical Industries, Ltd., $SiO_2$ content: 30% by weight) as an aqueous silica sol solution in such respective proportions that Al/(Si+Al)=10 mole % and Mg/(Si±Mg)=10 mole %, and thereafter, they were spray dried in a spray dryer set at a temperature of 130° C. to obtain a spherical carrier having an average particle size of 60 μm. It was calcined at 300° C. and then at 600° C. Thereafter, this was used as a carrier and poured into an aqueous solution having dissolved therein 15% by weight of palladium chloride and 10% by weight of sodium chloride so that the palladium content became 5 parts by weight per 100 parts by weight of the carrier, the resulting mixture was maintained at 60° C. for 2 hours to completely adsorb and support Pd on the carrier, and the supernatant was then dumped. Subsequently, water and sodium acetate were added so that a 6% by weight aqueous sodium acetate solution was prepared, and lead acetate was added in a proportion of 4.2 parts by weight per 100 parts by weight of the carrier, after which hydrazine was dropwise added thereto in a proportion of 3 moles per mole of palladium with stirring at 90° C. The mixture was maintained at the same temperature for a further one hour to obtain a reduction catalyst (written as Pd5.OPb4.2/Mg, Al—$SiO_2$). The Pd/Pb supported composition ratio of the supported catalyst was 3/1.29 by atomic ratio and the X-ray diffraction angle (2θ) on the (111) face of the palladium/lead intermetallic compound was 38.620 degree.

Example 1

50 g of the catalyst of Reference Production Example 1 was placed in a stirring bath type reactor having a liquid phase portion of 400 ml equipped with a catalyst-separator in which a separation membrane (a flat membrane of A type zeolite obtained according to the method described in Chemical Engineering Symposiums, Vol. 41, pages 102–105 (1994) (the effective membrane surface area: 80 Cm$^2$, α=8, 000, Q=0.25) and a sintered filter made of stainless steel having a pore diameter of 2 μm were installed; a vacuum was applied to the opposite side of the separation membrane; and reaction was conducted while water was separated by the PV method. To the reactor were continuously fed a 33.3% by weight methacrolein/methanol solution in which lead acetate was dissolved so that the lead concentration in the fed starting material liquid became 10 ppm, at a rate of 0.336 liter/hr and a NaOH/methanol solution at a rate of 0.037 liter/hr (corresponding to an aldehyde concentration of about 30% by weight), and the methyl methacrylate (MMA)producing reaction was conducted while the amount of air was controlled so that the reaction temperature was 80° C., the reaction pressure was 5 kg/cm$^2$ and the outlet oxygen concentration was 4.0% (corresponding to an oxygen partial pressure of 0.20 kg/cm$^2$). The concentration of NaOH fed to the reactor was controlled so that the pH of the reaction mixture became 7.1. When 10 hours had elapsed, the reaction product was analyzed to find that the methacrolein conversion was 51.3% and the selectivity of methyl methacrylate was 93.8%. The water concentration of the recovered reaction mixture was 1.65% by weight and the MMA-producing rate per catalyst was 11.64 moles/h.Kg catalyst. When the reaction was continued for a further 100 hours, the methacrolein conversion was 51.0% and the selectivity of methyl methacrylate was 94.0% and the producing rate was 11.60 moles/h/Kg catalyst, and substantially no change of reaction performance was seen.

Comparative Example 1

In quite the same apparatus as in Example 1, except that the separation membrane was not installed, the reaction was conducted under the same conditions as in Example 1. When 10 hours had elapsed, the reaction product was analyzed to find that the methacrolein conversion was 29.8% and the selectivity of methyl methacrylate was 90.3%. The water concentration in the recovered reaction mixture was 3.25% by weight, and the methyl methacrylate-producing rate per catalyst was 6.5 moles/–h.Kg catalyst.

Example 2

Using an anionic polysaccharide membrane (effective membrane area: 14 cm$^2$) prepared by the method described in Example 1 of JP-A-60-129,104 as the separation membrane, 6 g of the catalyst of Reference Production Example 1 was placed in a stirring bath type reactor having a liquid phase portion of 50 ml equipped with a catalyst-separator in which a sintered filter made of stainless steel of 2 μm was installed, a vacuum was applied to the opposite side of the separation membrane and the reaction was carried out while water was separated by the PV method. To the reactor were continuously fed a 33.3% by weight methacrolein/methanol solution in which lead acetate was dissolved so that the lead concentration in the fed starting material liquid became 10 ppm, at a rate of 45 ml/hr and a NaOH/methanol solution at a rate of 5 ml/hr (corresponding to an aldehyde concentration of about 30%), and the MMA-producing reaction was conducted while the amount of air was controlled so that the reaction temperature was 80° C., the reaction pressure was 5 kg/cm$^2$ and the outlet oxygen concentration was 4.0% (corresponding to an oxygen partial pressure of 0.20 kg/cm$^2$). The NaOH concentration to be fed to the reaction was controlled so that the pH of the reaction mixture became 7.1. When 10 hours had elapsed, the reaction product was analyzed to find that the methacrolein conversion was 43.2% and the selectivity of methyl methacrylate was 91.0%. The water concentration in the recovered reaction mixture was 2.38% by weight and the methyl methacrylate-producing rate per catalyst was 9.5 moles/h.Kg catalyst. The reaction was continued for a further 20 hours. The methacrolein conversion was 42.6%, the selectivity of methyl methacrylate was 91.2% and the producing rate was 9.4 moles/h/Kg catalyst, and a constant reaction performance was maintained.

Example 3

The reaction was conducted in the same manner as in Example 1, except that acrolein was substituted for the methacrolein. When 10 hours had elapsed, the reaction product was analyzed to find that the acrolein conversion was 63.6% and the selectivity of methyl methacrylate was 92.2%. The water concentration in the recovered reaction mixture was 2.9% by weight and the methyl acrylate-producing rate per catalyst was 17.4 moles/h.Kg catalyst. When the reaction was continued for a further 100 hours, it was found that the acrolein conversion was 63.1%, the selectivity of methyl acrylate was 93.5%, the producing rate was 17.6 moles/h/Kg catalyst, and a constant reaction performance was maintained.

Example 4

The reaction was conducted in the same manner as in Example 3, except that n-butanol was substituted for the methanol and a method in which 10 ppm of lead and NaOH were dissolved in and fed to a part of the withdrawn reaction mixture to control the pH to 7 was adopted. When 10 hours had elapsed, the reaction product was analyzed to find that the acrolein conversion was 48.5% and the selectivity of n-butyl acrylate was 92.8%. The water concentration in the recovered reaction mixture was 1.97% by weight and the butyl acrylate-producing rate per catalyst was 13.4 moles/h.Kg catalyst. When the reaction was continued for a further 100 hours, it was found that the acrolein conversion was 47.3%, the selectivity of butyl acrylate was 93.5%, the producing rate was 13.2 moles/h/Kg catalyst, and a constant reaction performance was maintained.

Example 5

The reaction was conducted in the same manner as in Example 4, except that 2-ethylhexyl alcohol was substituted for the methanol. When 10 hours had elapsed, the reaction product was analyzed to find that the acrolein conversion was 38.9% and the selectivity of 2-ethylhexyl acrylate was 91.2%. The water concentration in the recovered reaction mixture was 1.3% by weight and the 2-ethylhexyl acrylate-producing rate per catalyst was 10.76 moles/h.Kg catalyst. When the reaction was continued for a further 100 hours, it was found that the acrolein conversion was 39.6%, the selectivity of methyl acrylate was 90.2%, the producing rate was 10.6 moles/h/Kg catalyst, and a constant reaction performance was maintained.

Example 6

The reaction was conducted in the same manner as in Example 3, except that ethyl alcohol was substituted for the methanol. When 10 hours had elapsed, the reaction product was analyzed to find that the acrolein conversion was 54.3% and the selectivity of ethyl acrylate was 93.4%. The water concentration in the recovered reaction mixture was 2.1% by weight and the ethyl acrylate-producing rate per catalyst was 15.1 moles/h.Kg catalyst. When the reaction was continued for a further 100 hours, it was found that the acrolein conversion was 53.9%, the selectivity of ethyl acrylate was 93.6%, the producing rate was 15.0 moles/h/Kg catalyst, and a constant reaction performance was maintained.

Example 7

The reaction was conducted in the same manner as in Example 1, except that ethyl alcohol was substituted for the methanol. When 10 hours had elapsed, the reaction product was analyzed to find that the methacrolein conversion was 46.3% and the selectivity of ethyl methacrylate was 92.2%. The water concentration in the recovered reaction mixture was 1.21% by weight and the ethyl methacrylate-producing rate per catalyst was 10.3 moles/h.Kg catalyst. When the reaction was continued for a further 100 hours, the reaction product was analyzed to find that the methacrolein conversion was 45.0%, the selectivity of ethyl methacrylate was 93.1%. The water concentration in the recovered reaction mixture was 1.26% by weight and the ethyl methacrylate-producing rate per catalyst was 10.1 moles/h.Kg catalyst.

Comparative Example 2

In the same apparatus as in Example 3, except that the separation membrane was not installed, the reaction was conducted under the same conditions as in Example 3. When 10 hours had elapsed, the reaction product was analyzed to find that the acrolein conversion was 35.1% and the selectivity of methyl acrylate was 88.1%. The water concentration in the recovered reaction mixture was 3.4% by weight and the methyl acrylate-producing rate per catalyst was 9.2 moles/h.Kg catalyst. When 100 hours had elapsed, the reaction product was analyzed to find that the acrolein conversion was 34.8% and the selectivity of methyl acrylate was 88.6%. The methyl acrylate-producing rate per catalyst was 9.2 moles/h.Kg catalyst.

Comparative Example 3

In the same apparatus as in Example 6, except that the separation membrane was not installed, the reaction was conducted under the same conditions as in Example 6. When 10 hours had elapsed, the reaction product was analyzed to find that the acrolein conversion was 28.1% and the selectivity of ethyl acrylate was 87.4%. The water concentration in the recovered reaction mixture was 2.9% by weight and the ethyl acrylate-producing rate per catalyst was 7.3 moles/h.Kg catalyst. When 100 hours had elapsed, the reaction product was analyzed to find that the acrolein conversion was 27.4% and the selectivity of ethyl acrylate was 87.8%. The ethyl acrylate-producing rate per catalyst was 7.2 moles/h.Kg catalyst.

Comparative Example 4

In the same apparatus as in Example 4, except that the separation membrane was not installed, the reaction was conducted under the same conditions as in Example 4. When 10 hours had elapsed, the reaction product was analyzed to find that the acrolein conversion was 24.5% and the selectivity of n-butyl acrylate was 87.6%. The water concentration in the recovered reaction mixture was 2.3% by weight and the n-butyl acrylate-producing rate per catalyst was 6.4 moles/h.Kg catalyst. When 100 hours had elapsed, the reaction product was analyzed to find that the acrolein conversion was 23.2% and the selectivity of n-butyl acrylate was 88.3%. The n-butyl acrylate-producing rate per catalyst was 6.1 moles/h.Kg catalyst.

Comparative Example 5

In the same apparatus as in Example 5, except that the separation membrane was not installed, the reaction was conducted under the same conditions as in Example 5. When 10 hours had elapsed, the reaction product was analyzed to find that the acrolein conversion was 20.2% and the selectivity of 2-ethylhexyl acrylate was 88.9%. The water concentration in the recovered reaction mixture was 2.0% by weight and the 2-ethylhexyl acrylate-producing rate per catalyst was 5.4 moles/h.Kg catalyst. When 100 hours had elapsed, the reaction product was analyzed to find that the acrolein conversion was 19.7% and the selectivity of 2-ethylhexyl acrylate was 89.5%. The 2-ethylhexyl acrylate-producing rate per catalyst was 5.2 moles/h.Kg catalyst.

Comparative Example 6

In Comparative Example 1, the reactivity after 10 hours was evaluated, and thereafter, 40 g of molecular sieve 4A which had been pulverized to 30–100 microns and calcined at 300° C. for 3 hours was added, and after 3 hours, the reaction product was analyzed to find that the methacrolein conversion was 55.2% and the selectivity of methyl acrylate was 93.4%. The water concentration in the recovered reaction mixture was 1.4% by weight and the methyl methacrylate-producing rate per catalyst was 12.5 moles/h.Kg catalyst. When 100 hours had elapsed, the reaction product was analyzed to find that the methacrolein conversion was 28.5% and the selectivity of methyl methacrylate was 90.2%. The water concentration in the reaction mixture was 3.3% by weight and the methyl methacrylate-producing rate per catalyst was 6.2 moles/h.Kg catalyst.

Industrial Applicability

According to the process of this invention, water can be stably and continuously removed from the reaction system. As a result, the selectivity of a methacrylic acid ester or an acrylic acid ester and the producing rate can be enhanced. Also, the process of this invention is such a simple process that the regeneration of the water-adsorbent is not required, so that the productivity for a long period of time is high, the reactor can be made small, and a small amount of catalyst is sufficient. Thus, this invention can improve greatly the economical efficiency of the production of a methacrylic acid ester or an acrylic acid ester and is very useful in industry.

What is claimed is:

1. A process for producing a methacrylic acid ester or an acrylic acid ester comprising: reacting methacrolein or acrolein with an alcohol and molecular oxygen in the presence of a catalyst comprising Pd; removing water with a separation membrane which can selectively permeate water from a mixed liquid of the alcohol and water.

2. The process according to claim 1, wherein the separation membrane is an inorganic membrane.

3. The process according to claim 2, wherein the inorganic membrane has a water-separation factor ($\alpha$) of at least 1,000 and a permeation flux (Q) of at least 0.01.

4. The process according to claim 2, wherein the inorganic membrane is an A type zeolite membrane.

* * * * *